(12) United States Patent
Bi

(10) Patent No.: US 8,375,771 B1
(45) Date of Patent: Feb. 19, 2013

(54) VISCOMETER FOR TESTING CEMENT RHEOLOGY

(76) Inventor: Hongfeng Bi, Houston, TX (US)

( * ) Notice: Subject to any disclaimer, the term of this patent is extended or adjusted under 35 U.S.C. 154(b) by 397 days.

(21) Appl. No.: 12/800,719

(22) Filed: May 21, 2010

(51) Int. Cl.
*G01N 11/14* (2006.01)
(52) U.S. Cl. ............................................. 73/54.33
(58) Field of Classification Search ............... 73/54.23, 73/54.01, 54.03, 54.28, 54.31, 54.32, 54.33, 73/54.34
See application file for complete search history.

(56) References Cited

U.S. PATENT DOCUMENTS

| | | |
|---|---|---|
| 3,239,325 A | 3/1966 | Roberson et al. |
| 3,435,666 A | 4/1969 | Fann |
| 4,466,276 A | 8/1984 | Ruyak et al. |
| 4,524,611 A | 6/1985 | Richon et al. |
| 4,534,209 A | 8/1985 | Sanders |
| 4,630,468 A | 12/1986 | Sweet |
| 4,633,708 A | 1/1987 | Blommaert |
| 4,653,313 A | 3/1987 | Sabins et al. |
| 4,736,624 A | 4/1988 | Arnstein et al. |
| 4,823,594 A | 4/1989 | Gray |
| 5,874,666 A | 2/1999 | Bishop |
| 6,938,464 B1 | 9/2005 | Bi |
| 6,951,127 B1 | 10/2005 | Bi |
| 7,287,416 B1 | 10/2007 | Bi |
| 7,412,877 B1 * | 8/2008 | Bi ............................... 73/54.28 |

* cited by examiner

*Primary Examiner* — Hezron E Williams
*Assistant Examiner* — Nathaniel Kolb

(57) ABSTRACT

Viscometer (80) with a closed bottom rotor assembly (51) rotatable by a coupling magnet (34) and a driving magnet (38) to shear a tested fluid thus imparting torque to a bob (30) mounted on a bob shaft (24) supported via bearings (22 and 18) inside rotor assembly (51). An upper chamber (96) located in the upper portion of rotor assembly (51) is at least partially filled with sample and communicates pressure with lower portion of rotor assembly (51) and rotor top via small gap (106) and small gap (110). A spiral spring (70) restricts the rotation of bob shaft (24). Magnetometer (10) measures the angular position of a top magnet (72) connected to the top of bob shaft (24). This angular position information is further converted to the viscosity of the tested fluid.

18 Claims, 2 Drawing Sheets

VISCOMETER FOR TESTING CEMENT RHEOLOGY

CROSS-REFERENCE TO RELATED APPLICATIONS

Not applicable.

BACKGROUND

1. Field of Invention

The present invention relates to a low maintenance high pressure viscometer configured for the study of a cement of the inorganic, organic or mixed type.

2. Description of Prior Art

Drilling oil and geothermal wells requires the use of well cements. In wells, particularly petroleum wells, it is necessary to inject a liquid cement between a metal casing and the ground formation bordering the borehole. The setting of the liquid cement isolates the various layers of the ground formation around the borehole and holds the casing in place. For successful cementing it is important to use a liquid cement having a clearly determined rheological profile in order to determine true "pumpability time" (or setting time). Too short a time would result in premature clogging, and too long a time would needlessly delay resumption of work after cementing. Thus, for development and testing of well cements, pressure vessels are required to simulate downhole conditions accurately and repeatably. A rheometer configuration to enable cement testing of this kind makes it possible to follow the rheological changes over time of a progressively hardening material under conditions very close to the real conditions likely to be encountered downhole.

However, when testing cement samples, standard rheometer hardware (such as that as shown in U.S. Pat. No. 7,412,877) is prone to undesirably long test setup times, as well as extended cleanup and maintenance times, and can even become damaged when testing fluids such as cements as the cement sets or becomes solid. U.S. Pat. No. 4,653,313 describes a container for testing cement sample under pressure. However, this configuration would not provide sensitive and accurate measurement because of the friction between the central shaft and the seal around it. As a matter of fact, any seal directly in contact with the moving torque measurement parts would cause a considerable number of measurement errors due to friction.

Therefore, it is an object of this invention to provide a viscometer configuration allowing the rheological testing of cements under conditions closely simulating downhole conditions while avoiding contamination of cement samples with pressurization fluid.

It is another object of this invention to provide a viscometer configuration that requires substantially less maintenance work than would normally be necessary when testing cements, yet meets industry standards of accuracy, reliability, durability, dependability, repeatability, and ease of cleaning.

SUMMARY

A viscometer configuration in accord with the present invention comprises a pressure vessel inside which a rotor assembly is mounted on a pivot while a magnetic coupling for rotating the rotor is mounted outside the vessel. The interior of said rotor assembly is largely isolated from said pressure cell except for small gaps in the rotor assembly. Suspended within the rotor assembly is a bob capable of angular motion about the longitudinal axis of the rotor. The device is constructed so that the bob is immersed in a cement sample, the rheological changes of which are to be measured. The bob is suspended within the rotor by a bob shaft and is functionally protected from contamination with pressurization fluid. A spiral spring permits limited angular motion of the bob shaft. A magnet is secured on top of the bob shaft. A magnetometer located on the top of the pressure vessel senses the rotation of the magnet.

The apparatus and method of the present invention provide a way to measure the shear stress property of cement samples under shear conditions.

DRAWING FIGURES

Other objects, features and advantages will be apparent from the following detailed description of preferred embodiments taken in conjunction with accompanying drawings in which.

REFERENCE NUMERALS IN DRAWINGS

| | | | |
|---|---|---|---|
| 10 | magnetometer | 10A | magnetometer |
| 12 | inlet | 12A | inlet |
| 13A | top jewel bearing | 14 | set screw |
| 14A | set screw | 15A | top sleeve |
| 16 | spring holder | 16A | spring holder |
| 18 | bob shaft bearing | 19 | small gap |
| 20 | bearing spacer | 21A | sample injection hole |
| 22 | bob shaft bearing | 24 | bob shaft |
| 24A | bob shaft | 26 | o-ring |
| 26A | o-ring | 30 | bob |
| 30A | bob | 31 | sample |
| 31A | sample | 32 | bearing |
| 32A | jewel bearing | 33 | thread |
| 33A | thread | 34 | coupling magnet |
| 34A | coupling magnet | 35 | cell wall |
| 35A | cell wall | 38 | driving magnet |
| 38A | driving magnet | 39 | thermal couple |
| 39A | thermal couple | 40 | magnet mount |
| 40A | magnet mount | 41 | straight bore |
| 41A | straight bore | 42 | bearing |
| 42A | bearing | 43 | conical surface |
| 43A | conical surface | 44 | bearing |
| 44A | bearing | 46 | lock nut |
| 46A | lock nut | 47 | cell bottom |
| 47A | cell bottom | 51 | rotor assembly |
| 51A | rotor assembly | 52 | heater |
| 52A | heater | 54 | pivot |
| 54A | pivot | 56 | rotor wall |
| 56A | rotor wall | 57A | jewel bearing |
| 59 | conical surface | 61 | venting hole |
| 63 | screw thread | 63A | screw thread |
| 64 | snap ring | 66 | bearing holder |
| 66A | bearing holder | 67 | flat |
| 67A | flat | 68 | snap ring |
| 70 | spiral spring | 70A | spiral spring |
| 72 | top magnet | 72A | top magnet |
| 74 | outlet | 74A | outlet |
| 76 | cell cap | 76A | cell cap |
| 78 | thread | 78A | thread |
| 80 | viscometer | 80A | viscometer |
| 90A | pin | 94 | rotor cover |
| 94A | rotor cover | 96 | chamber |
| 96A | chamber | 98 | rubber diaphragm |
| 98A | rubber diaphragm | 100 | rotor bottom |
| 100A | rotor bottom | 102 | o-ring |
| 102A | o-ring | 104 | collar |
| 104A | collar | 106 | small gap |
| 106A | gap | 107 | thread |

-continued

| | | | |
|---|---|---|---|
| 107A | thread | 108 | lock ring |
| 108A | lock ring | 110 | small gap |
| 110A | small gap | 112 | set screw |
| 112A | set screw | | |

DESCRIPTION

Figure 1:
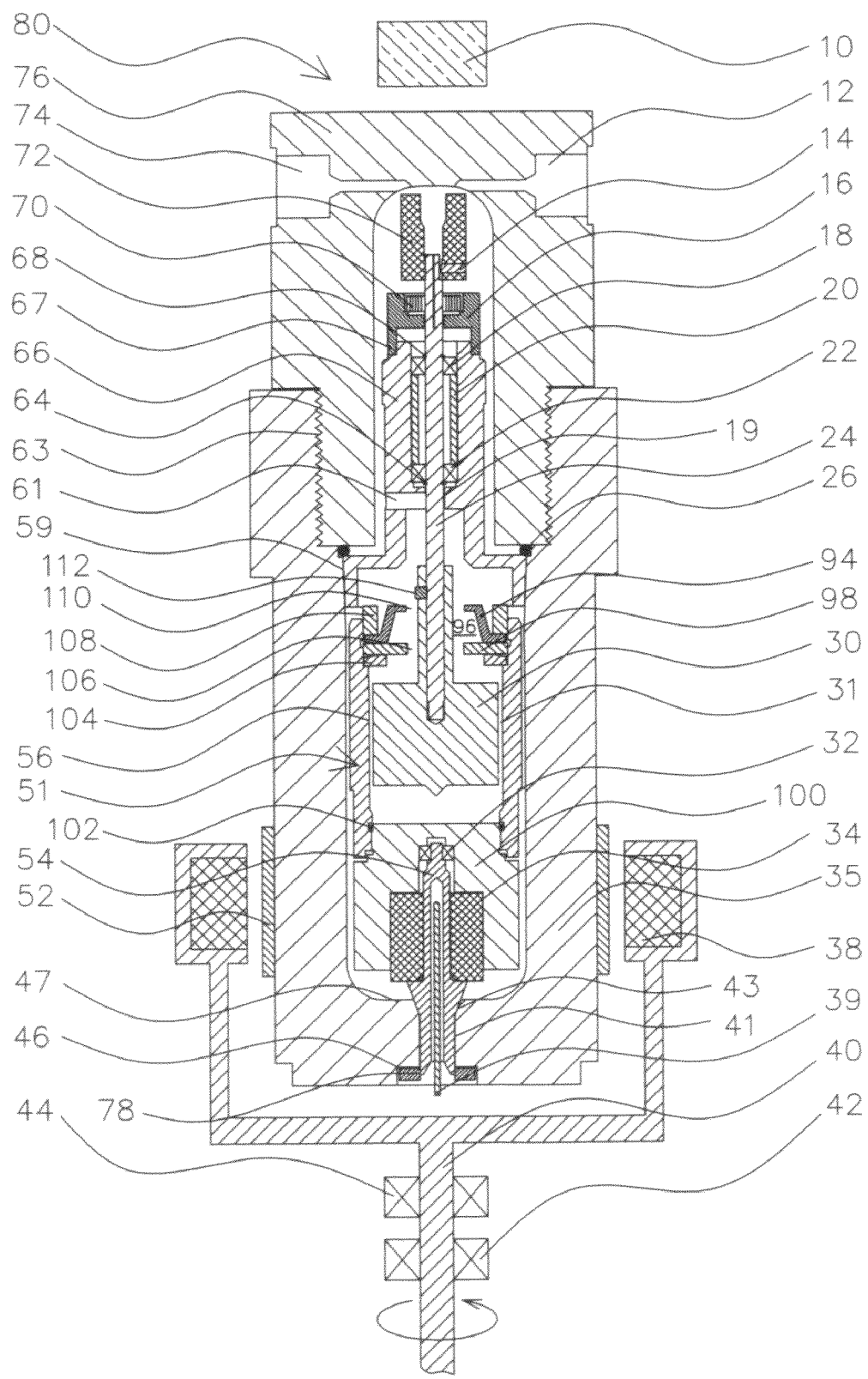
FIG. 1 is a cross-section view of a preferred embodiment of the invention.

FIG. 1—Preferred Embodiment

FIG. 1 is a cross-section view of a viscometer 80 with a cylindrical cell wall 35 and a cylindrical cell cap 76. Cell wall 35 is detachable from cell cap 76 via a screw thread 63. An o-ring 26 assures against the escape of fluid through screw thread 63. Inside of cell wall 35 and below screw thread 63 is a conical surface 59 with reduced diameter, below which cell wall 35 extends downward to a cell bottom 47. A tapered hole with a conical surface 43 and a straight bore 41 is located in the center of cell bottom 47. A pivot 54, which is secured to cell bottom 47 by a lock nut 46 through a thread 78, is seated into said tapered hole on conical surface 43. Lock nut 46 is tightened to provide initial seal on straight bore 41 between cell bottom 47 and pivot 54. A thermal couple 39 is inserted into the center of pivot 54.

A bearing 32 and a coupling magnet 34 are positioned inside a rotor bottom 100. Rotor bottom 100 is attached to a rotor wall 56 via a thread 33, forming the outer structure of rotor assembly 51. An o-ring 102 ensures against fluid leakage from the junction of a rotor wall 56 and rotor bottom 100. Rotor assembly 51 is placed onto pivot 54 so that it rests on top of bearing 32, so that bearing 32 provides vertical support of rotor assembly 51 and enables it to rotate freely on the same axis as pivot 54.

A bob 30 is placed inside rotor wall 56. A collar 104 is placed radially around the shaft of bob 30 so that it rests inside rotor wall 56. A rubber diaphragm 98 is placed on top of the collar 104. Rubber diaphragm 98 is shaped to allow a small gap 106 between the interior edge of rubber diaphragm 98 and bob 30. A rotor cover 94 is placed on top of the rubber diaphragm 98. A lock ring 108 is attached to the top of rotor wall 56 via a thread 107.

A bearing holder 66 consists of a conical section and two different outside diameter sections. The outer surface of the conical section of bearing holder 66 mates inside conical surface 59 of cell wall 35. An o-ring 26 provides a liquid-tight seal on conical surface 59. A bob shaft 24 passes through the center of bearing holder 66 and is rotationally supported by a bob shaft bearing 18, a bob shaft bearing 22, a bearing spacer 20, a snap ring 68 and a snap ring 64.

A machined flat 67 is provided on the top of bearing holder 66. Mating and resting on flat 67 is a spring holder 16. A spiral spring 70 is placed in the center of spring holder 16 so that the outside lead of spiral spring 70 is fixed to the inside counter bore of spring holder 16 and the inside lead of spiral spring 70 is fixed to bob shaft 24 with any conventional means. A horseshoe-type top magnet 72 is fixed to the top of bob shaft 24 with a set screw 14. Additionally, a small gap 110 channels from the top of bearing holder 66 to a chamber 96. A sample 31 is injected into chamber 96 and fills all of the space inside rotor wall 56. A venting hole 61 connects the outer surface of bearing holder 66 to a small gap 19 between bob shaft 24 and bearing holder 66. A set screw 112 mounted inside the shaft of bob 30 can be tightened to attach the bob shaft 24 to the bob 30.

An inlet 12 and an outlet 74 provide ports for applying and releasing pressure. A magnetometer 10 located on the top of cell cap 76 can measure the rotational displacement of top magnet 72.

A magnet mount 40 is rotationally supported on the outside of cell wall 35 by a bearing 42 and a bearing 44. Magnet mount 40 can be rotated by any conventional means such as a gear box or motor. A pair of driving magnet 38 is mounted on magnet mount 40 at considerably the same level where coupling magnet 34 is mounted inside of the cell wall 35. Heat is provided by a heater 52.

OPERATION

FIG. 1—Preferred Embodiment

Begin assembly of viscometer 80 by inserting pivot 54 into cell bottom 47 through the conical hole with straight bore 41 and conical surface 43. Secure pivot 54 to cell bottom 47 by screwing lock nut 46 onto thread 78. Pivot 54 and cell bottom 47 can be cleaned together with cell wall 35. Insert thermal couple 39 up into pivot 54.

Install bearing 32 and coupling magnet 34 into the rotor bottom 100. Install o-ring 102 into the lower end of rotor wall 56, then attach rotor bottom 100 to rotor wall 55 via thread 33, thus forming the outer structure of rotor assembly 51. Holding bob 30 by the stem, lower it inside the top of rotor assembly 51 so that it fits just inside rotor wall 56, then place collar 104 and rubber diaphragm 98 inside rotor assembly 51, on top of bob 30. Pour sample 31 into rotor assembly 51 until it submerges rubber diaphragm 98. Put rotor cover 94 inside rotor assembly 51, on top of bob 30 and use a syringe to inject sample 31 into chamber 96 via small gap 110 until chamber 96 is full. Screw lock ring 108 onto rotor assembly 51 via thread 107.

Holding bob shaft 24 in hand, install bob shaft bearing 18, bearing spacer 20, bob shaft bearing 22, snap ring 68 and snap ring 64 onto bob shaft 24. Then vertically insert this subassembly into bearing holder 66. Next, install spring holder 16 and spiral spring 70 onto the top of bearing holder 66, resting spring holder 16 on flat 67 at the top of bearing holder 66. Secure top magnet 72 to the top of bob shaft 24 via set screw 14. Attach bob 30 onto bob shaft 24 bottom via set screw 112. Then vertically push this bob shaft holder assembly down into cell wall 35 slowly, so that the bearing 32 inside of rotor bottom 100 rests on top of the pivot 54 and the whole assembly is able rotate on top of the pivot freely.

Using screw thread 63, screw down cell cap 76 with o-ring 26 in place. Pump pressurization fluid from inlet 12 until all air inside of pressure vessel is expelled out through outlet 74. Sample testing pressure can be raised by pumping more pressurization fluid into pressure vessel or releasing some pressurization fluid from pressure vessel.

It is very important to have rotor assembly 51 and bob 30 concentrically aligned. Conical surface 59 is machined with high precision to ensure bob 30 is concentrically aligned with rotor assembly 51. This conical surface 59 also significantly simplifies the installation process since no addition adjustment or screw turning is required to ensure the good concentricity between rotor assembly 51 and bob 30.

A motor or gearbox drives magnet mount 40 to rotate on bearing 42 and bearing 44, carrying driving magnet 38. A heater 52 heats up cell wall 35 while thermal couple 39 provides temperature feedback for temperature control. Due to the magnetic coupling between driving magnet 38 and coupling magnet 34, rotor assembly 51 rotates at the same revolving speed as magnet mount 40 does. Because of the viscosity of the tested sample, a torque is generated on bob 30, causing it to rotate. Because of spiral spring 70, the rotation angle of bob shaft 24 is roughly proportional to the torque applied on bob 30. Magnetometer 10 picks up the rotation angle of top magnet 72 which rotates with bob shaft 24. The rotation angle in turn can be used to calculate the viscosity of tested sample.

One of the drawbacks of most liquid pressurized viscometers is the mixing between tested sample and pressurization fluid. If a seal is provided between pressurization fluid and tested sample, the seal will induce friction errors causing inaccurate measurement. If pressurization fluid is allowed to contact tested sample directly, pressurization fluid will mix with tested sample because of stirring and the compressibility of tested sample.

In the current invention, when pressurization fluid is introduced, the sample fluid level is pushed down due to the compressibility of tested sample. Thus, some of the pressurization fluid goes down through small gap 19 and enters chamber 96 through small gap 110. However, chamber 96 is large enough so that at maximum rated pressure, chamber 96 is still at least half filled with sample fluid. This ensures the accuracy of the measurement because the measurement zone below collar 104 is always totally filled with sample fluid.

Additionally, because collar 104 separates lower measurement zone and chamber 96, fluid inside of chamber 96 is relatively static. Thus no stirring could cause mixing between pressurization fluid and tested sample if the interface between pressurization fluid and tested sample is inside of chamber 96.

The pressurization fluid should be chosen carefully. This pressurization fluid should not spontaneously dissolve into or mix with the tested sample, and should have a specific gravity lower than the specific gravity of the sample. Pressurization fluid communicates pressure with sample fluid through venting hole 61 and small gap 110 and small gap 106 while keeping bob shaft bearing 18 and bob shaft bearing 22 submerged. Because pressurization fluid is generally a clean, nonabrasive liquid, this ensures bob shaft bearing 18 and bob shaft bearing 22 rotate freely and have a long working life span. If conventional type of bearings, such as roller bearings, ball bearings or spherical bearings are used in a comparative viscometer without a mechanism preventing sample mixing with pressurization fluid, those bearings will quickly stop working properly, normally with excessive drag, because tested sample is normally filled with a lot of fine solid contents.

If a cement sample is left to set inside the rotor assembly 51, said assembly can be completely disassembled so that the cement sample can be pushed out of the rotor wall 56 quickly and the rotor assembly 51 components can be cleaned easily.

DESCRIPTION

Figure 2:
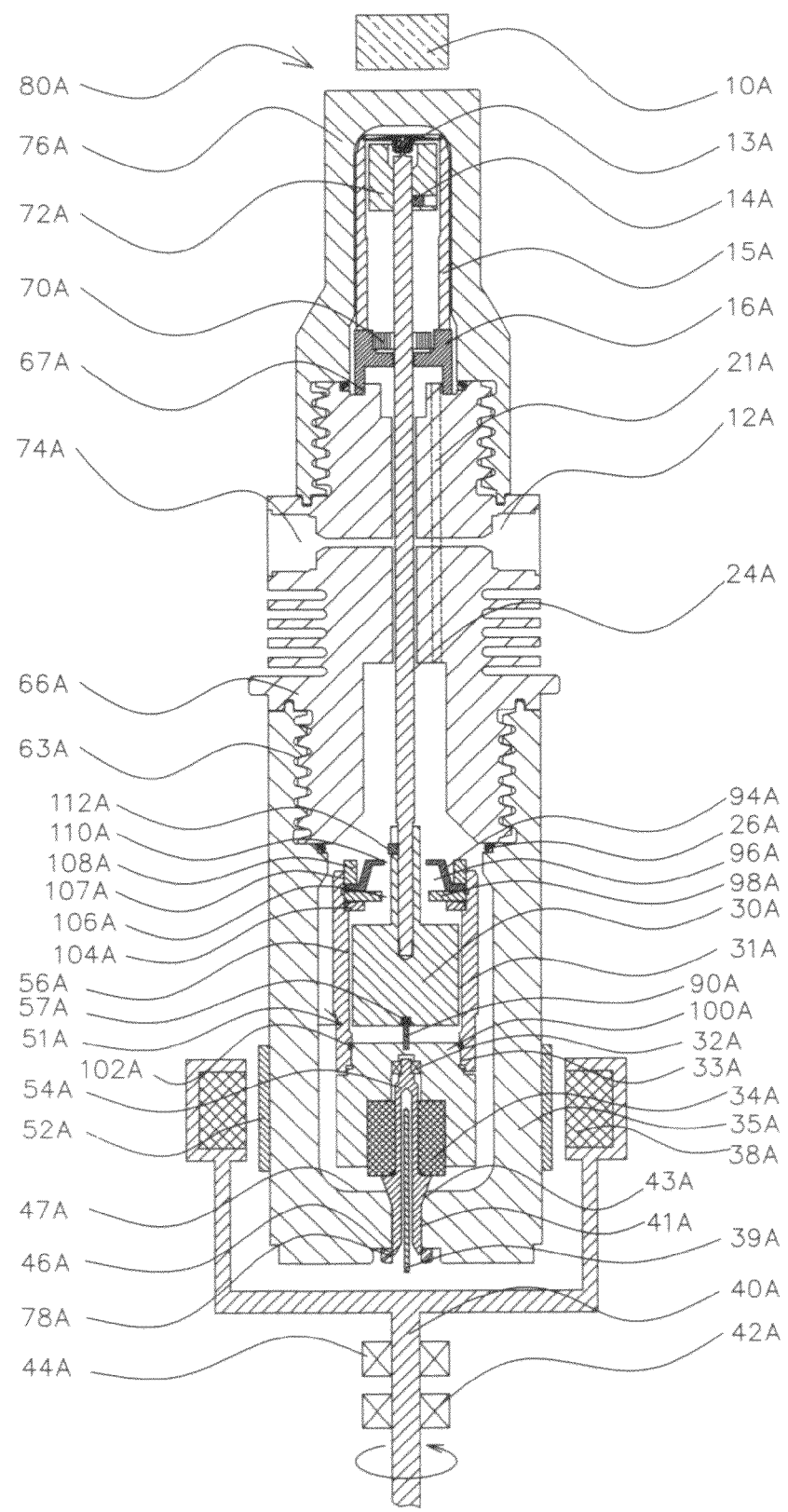
FIG. 2 is an alternative embodiment with jewel bearings and three-piece pressure vessel configuration.

FIG. 2—An Alternative Embodiment with Jewel Bearings and Three-Piece Pressure Vessel Configuration FIG. 2 is a cross-section view of a viscometer 80A with a cell wall 35A, a bearing holder 66A and a cell cap 76A. Cell wall 35A is detachable from bearing holder 66A via a screw thread 63A and cell cap 76A is screwed on top of bearing holder 66A. An o-ring 26A assures against escape of fluid through screw thread 63A.

Cell wall 35A extends downward to a cell bottom 47A, where a tapered hole with a conical surface 43A and a straight bore 41A is located in the center of cell bottom 47A. A pivot 54A, which is secured to cell bottom 47A by a lock nut 46A through a thread 78A, is seated into said tapered hole through straight bore 41A. Lock nut 46A is tightened to provide initial seal on conical surface 43A between cell bottom 47A and pivot 54A. A thermal couple 39A is inserted into the center of pivot 54A. Radially outward of the outer surface of pivot 54A is a coupling magnet 34A.

A jewel bearing 32A is fitted into a rotor bottom 100A. When rotor bottom 100A is placed on top of pivot 54A, jewel bearing 32A allows it to rotate freely on the same central axis of pivot 54A.

A rotor wall 56A is attached to rotor bottom 100A via a thread 33A, forming the outer structure of rotor assembly 51A. An o-ring 102A assures against escape of fluid from between rotor wall 56A and rotor bottom 100A. These components can rotate freely on the same central axis of pivot 54A.

A bob shaft 24A passes through the center of bearing holder 66A while not in contact with its inside bore directly. A machined flat 67A is provided on the top of bearing holder 66A. Mating and resting on flat 67A is a spring holder 16A. A spiral spring 70A is placed in the center of spring holder 16A so that the outside lead of spiral spring 70A is fixed to the inside counter bore of spring holder 16A and the inside lead of spiral spring 70A is fixed to bob shaft 24A with any conventional means.

Resting on top of spring holder 16A is a top sleeve 15A, on which a top jewel bearing 13A is mounted. The tip of bob shaft 24A is in contact with top jewel bearing 13A. Bob shaft 24A is secured to a bob 30A by a set screw 112A.

Bob 30A is positioned inside rotor wall 56A. Directly above bob 30A, inside rotor wall 56A, is a collar 104A. A rubber diaphragm 98A is placed above collar 104A, and a rotor cover 94A is placed above rubber diaphragm 98A. A small gap 106A allows fluid to flow between the area around bob 30A and a chamber 96A, which is inside rotor cover 94A. Fluid can also flow into chamber 96A through small gap 110A and into the lower assembly surrounding the bob 30A through a small gap 106A. A lock ring 108A is fixed to the top of rotor assembly 51A via a thread 107A, above rotor cover 94A. A pin 90A is set into the center of the top of rotor bottom 100A. Pin 90A fits into a jewel bearing 57A which is set into the center of the bottom of bob 30A. Jewel bearing 57A and top jewel bearing 13A support the bob shaft 24A and allow it to rotate.

A horseshoe type top magnet 72A is also fixed to the top of bob shaft 24A with a set screw 14A. A sample 31A is injected into a sample injection hole 21A and fills the area above the rotor assembly 51A.

An inlet 12A and an outlet 74A provide ports for applying and releasing pressure. A magnetometer 10A located on the top of cell cap 76A can measure the rotational displacement of top magnet 72A.

A magnet mount 40A is rotationally supported on the outside of cell wall 35A by a bearing 42A and a bearing 44A. Magnet mount 40A can be rotated by any conventionally means such as gear box or motor. A pair of driving magnet 38A is mounted on magnet mount 40A at considerably the same level where coupling magnet 34A is mounted inside of the cell wall 35A. Heat is provided by a heater 52A.

OPERATION

FIG. 2—An Alternative Embodiment with a Jewel Bearing and Three-Piece Pressure Vessel Configuration Begin assembly of viscometer 80A by inserting pivot 54A into cell bottom 47A through the conical hole with straight bore 41A and conical surface 43A. Secure pivot 54A to cell bottom 47A by screwing lock nut 46A onto thread 78A. Pivot 54A and cell bottom 47A can be cleaned together with cell wall 35A. Insert thermal couple 39A up into pivot 54A. Place coupling magnet 34A onto pivot 54A so that it is positioned radially outward from pivot 54A.

Install o-ring 102A into rotor wall 56A, then attach rotor wall 56A to rotor bottom 100A via thread 33A, thus forming the outer structure of rotor assembly 51A. Install jewel bearing 32A into rotor bottom 100A. Insert pin 90A into the top of rotor bottom 100A.

Install jewel bearing 57A into the bottom of bob 30A. Drop bob 30A into rotor assembly 51A so that it fits inside rotor wall 56A and the jewel bearing 32A rests on the pin 90A. Drop collar 104A into rotor wall 56A, and drop rubber diaphragm 98A on top of collar 104A. Drop rotor cover 94A on top of diaphragm 98A, and fasten lock ring 108A onto the top of rotor wall 56A via thread 107A.

Insert bob shaft 24A into bearing holder 66A. Attach spring holder 16A and spiral spring 70A onto the top of bearing holder 66A, resting on the flat 67A. Install the top sleeve 15A onto the top of bearing holder 66A, so that bob shaft 24A is centered by top jewel bearing 13A. Attach top magnet 72A to the top of bob shaft 24A using set screw 14A. Fasten bob 30A onto the bottom of bob shaft 24A with set screw 112A. Pour test sample 31A into cell wall 35A so that the sample surface just submerges the top of pivot 54A.

Screw bearing holder 66A, with attached bob shaft assembly, onto cell wall 35A using thread 63A. O-ring 26A ensures against fluid leakage here. Rotor bottom 100A should be rotationally supported by jewel bearing 32A mounted on top of pivot 54A. As it is lowered, bob 30A will sink into the sample fluid, causing the sample fluid level to rise. A syringe is used to inject additional sample fluid through small injection hole 21A to bring sample fluid level up so that sample fluid totally fills the area above the rotor assembly 51A.

Finally, screw down cell cap 76A onto bearing holder 66A. Pump pressurization fluid from inlet 12A. Sample testing pressure can be raised by pumping more pressurization fluid into pressure vessel through inlet 12 or releasing some pressurization fluid from pressure vessel through outlet 74A.

A motor or gearbox mounted on bearing 42A and bearing 44A drives magnet mount 40A to rotate carrying driving magnet 38A. A heater 52A heats up cell wall 35A while thermal couple 39A provides temperature feedback for temperature control. Due to the magnetic coupling between driving magnet 38A and coupling magnet 34A, rotor assembly 51A rotates at the same revolving speed as magnet mount 40A does. Because of the viscosity of tested sample, a torque is generated on bob 30A causing it to rotate. Because of spiral spring 70A, the rotation angle of bob shaft 24A is roughly proportional to the torque applied on bob 30A. Magnetometer 10A picks up the rotation angle of top magnet 72A which rotates with bob shaft 24A. The rotation angle in turn can be used to calculate the viscosity of tested sample.

In this embodiment, when pressurization fluid is applied, the sample fluid level is pushed down due to the compressibility of tested sample. Thus initial sample fluid goes down to the area above the rotor assembly 51A through inlet 12A, and into chamber 96A through small gap 110A and into the rotor assembly 51A through small gap 106A. However, chamber 96A is large enough so that at maximum rated pressure, chamber 96A is still at least half filled with sample fluid. This ensures the accuracy of the measurement because measurement zone below collar 104A is always totally filled with sample fluid. Additionally, because collar 104A separates lower measurement zone and chamber 96A, fluid inside of chamber 96A is relatively static. Thus no stirring could cause the mixing between pressurization fluid and tested sample if the interface between pressurization fluid and tested sample is inside of chamber 96A.

RAMIFICATIONS

Bob 30 does not have to be cylindrical shape. It could be a blade, frame or any geometry shape.

Bob shaft bearing 18 and bob shaft bearing 22 could be combined as one needle bearing or equivalent bearing with low friction.

Rotor assembly 51 does not have to be driven with a magnetic coupling across cell wall 35. Rotor assembly 51 could be driven to rotate with any means such as directly driven at the bottom of the cell body with dynamic seal, etc.

Spiral spring 70 could be helical spring or other types of equivalent resilient mechanism.

There are many other ways to measure the angular displacement of bob shaft 24. For example, in preferred embodiment viscometer 80, top magnet 72 and magnetometer 10 can be replaced with a pair of concentrically mounted electrical stator and rotor to measure the rotation of bob shaft 24. Additionally, top magnet 72 and magnetometer 10 can be replaced with an encoder to measure the rotation of bob shaft 24. A potentiometer and a brush attached to bob shaft 24 could measure the rotation as well.

Alternatively, a metal arm or wiper which rotates with bob shaft 24, and a wire-wound conductance transducer which is mounted directly or indirectly on bearing holder 66 or cell cap 76, can also be used to measure the rotation of bob shaft 24 by measuring the conductance change in the wire-wound coil.

Rotor cover 94 and rubber diaphragm 98 could be attached from bob shaft 24 and rotate together with bob shaft 24. In this case, their outside edge will be separated from rotor assembly 51 by small gaps to reduce pressurization fluid mixing with tested sample using the same working principle described in this invention.

Pressurization media used to pressurize viscometer 80 can be any high pressure gas or any liquid fluids that do not dissolve into tested sample and have a density smaller than tested sample.

CONCLUSION, AND SCOPE

Accordingly, the reader will see that this invention can be used to construct a high pressure viscometer for accurate and repeatable measurement of cement rheology. The configuration enables simple operation procedure and low maintenance.

OBJECTS AND ADVANTAGES

From the description above, a number of advantages of my viscometer become evident:
  (a) Due to conventional low friction ball bearings design, current invention substantially reduces operation cost comparing to jewel bearing designs. It had been unsuccessful to use conventional ball bearings in liquid pressurized high pressure viscometer because any fine solids in tested sample would cause low friction ball bearings to fail. Also because ball bearings are much durable than jewel bearings, maintenance task is reduced significantly.
  (b) Totally eliminate the measurement error because of sample mixing with pressurization fluid in a comparative viscometer.

(c) Very conveniently isolate all electrical component from pressurized zone thus reducing maintenance work.

(d) Very compact design by using small size spiral spring.

(e) Extremely simple installation and disassembly procedures due to conical bearing holder design while maintaining high concentricity between bob and rotor.

Further objects and advantages of my invention will become apparent from a consideration of the drawings and ensuing description.

The invention claimed is:

1. A pressurized viscometer or consistometer comprising:
   (a) a pressure vessel,
   (b) a pressurization medium of a first density to pressurize said pressure vessel,
   (c) a sample of a second density to be tested,
   (d) within said pressure vessel a container is submerged in said pressurization medium inside of said pressure vessel,
   (e) said container is consists of at least a lower chamber filled with said sample, and at least an upper chamber which is at least partially filled with said sample,
   (f) said upper chamber has reduced openings positioned between said container top and said chamber for communicating pressure within said pressure vessel,
   (g) whereby said pressurization medium would not mix with said sample because of the nature of their density difference.

2. A viscometer comprising:
   (a) a pressure vessel,
   (b) a pressurization medium of a first density to pressurize said pressure vessel,
   (c) within said pressure vessel a container submerged in said pressurization medium is driven to rotate and consists of at least a lower chamber filled with a sample of a second density to be tested, and at least an upper chamber which is at least partially filled with said sample,
   (d) within said upper chamber said container has reduced openings positioned between said container top and said lower chamber for communicating pressure within said pressure vessel,
   (e) whereby said pressurization medium would not mix with said sample because of the nature of their density difference,
   (f) a bob within said lower chamber.

3. A viscometer according to claim 2 further comprising a bearing means for rotationally suspending said bob.

4. The viscometer of claim 3 wherein said bearing means are low friction ball bearings or roller bearings.

5. The viscometer of claim 3 wherein said bearing means are low friction jewel bearings.

6. A viscometer according to claim 3 further comprising a spring means restricting the rotation of said bob.

7. The viscometer of claim 6 wherein said spring means is a spiral spring.

8. The viscometer of claim 6 wherein said spring means is a helical spring.

9. A viscometer according to claim 6 further comprising means for directly or indirectly sensing the rotation of said bob.

10. The viscometer of claim 9 wherein said means for directly or indirectly sensing the rotation of said bob consist of a magnet and a magnetometer.

11. The viscometer of claim 9 wherein said means for directly or indirectly sensing the rotation of said bob consist of a potentiometer and a brush.

12. The viscometer of claim 2 wherein said means for driving said container to rotate is a magnetic coupling across said pressure vessel wall.

13. The viscometer of claim 2 wherein said bob is cylindrical shape.

14. A viscometer according to claim 2 further comprising a bob suspension means comprising at least one conical outer surface part mating another conical surface which is directly or indirectly associated to said pressure vessel.

15. The viscometer of claim 2 wherein said upper chamber is formed by at least two disc shaped fins disposed in parallel along the axial direction that said bob rotates.

16. The viscometer of claim 15 wherein said two disc shaped fins have their outside diameters connected to said container and said two disc shaped fins are not directly in contact with other static mechanical components.

17. The viscometer of claim 15 wherein said two disc shaped fins having their inside diameters connected to a bob suspension means while their outside diameters separated from said container and any component that rotates together with said container.

18. The viscometer of claim 2 wherein said bob is a hollow shape with at least one opening allowing the flow of sample through said bob.

* * * * *